(12) United States Patent
Pigamo et al.

(10) Patent No.: US 8,536,386 B2
(45) Date of Patent: Sep. 17, 2013

(54) PROCESS FOR THE PREPARATION OF FLUOROOLEFIN COMPOUNDS

(75) Inventors: Anne Pigamo, Francheville (FR); Michel Devic, Sainte Foy les Lyon (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 212 days.

(21) Appl. No.: 12/602,705

(22) PCT Filed: Aug. 18, 2009

(86) PCT No.: PCT/FR2009/051594
§ 371 (c)(1),
(2), (4) Date: May 2, 2011

(87) PCT Pub. No.: WO2010/029239
PCT Pub. Date: Mar. 18, 2010

(65) Prior Publication Data
US 2011/0201852 A1    Aug. 18, 2011

(30) Foreign Application Priority Data
Sep. 11, 2008  (FR) ...................................... 08 56112

(51) Int. Cl.
*C07C 17/00* (2006.01)
(52) U.S. Cl.
USPC ........................................................ 570/155
(58) Field of Classification Search
USPC ........................................................ 570/155
See application file for complete search history.

(56) References Cited

U.S. PATENT DOCUMENTS

| 6,403,846 | B1 | 6/2002 | Sekiva et al. |
| 6,548,719 | B1 | 4/2003 | Nair et al. |
| 2007/0112230 | A1* | 5/2007 | Mukhopadhyay et al. ... 570/161 |
| 2009/0234165 | A1 | 9/2009 | Chiu et al. |
| 2010/0029997 | A1* | 2/2010 | Wang et al. .................. 570/134 |
| 2010/0190554 | A1 | 7/2010 | Gagner et al. |

FOREIGN PATENT DOCUMENTS

| WO | WO 2007/056194 | 5/2007 |
| WO | WO 2008/075017 | 6/2008 |

OTHER PUBLICATIONS

Knunyants et al., Reactions of Fluoroolefins, Communication 13 Catalytic Hydrogenation of Perfluoroolefins, Journal of the USSR Academy of Sciences, Chemisrty Dept., 1959, pp. 1312-1318.
Chretien, A., et al., Nouveau Traite de Chimie Minerale, 1963, pp. 50-53.

* cited by examiner

*Primary Examiner* — Jafar Parsa
(74) *Attorney, Agent, or Firm* — Buchanan Ingersoll & Rooney P.C.

(57) ABSTRACT

A subject-matter of the invention is a process for the preparation of fluoroolefin compounds. It relates more particularly to a process for the manufacture of a compound of formula (I) $CF_3$—$CF$=$CHX$ in which X represents a hydrogen or fluorine atom, comprising at least one stage of dehydrofluorination of a compound of formula (II) $CF_3$—$CHF$—$CHFX$ during which the compound of formula (II) is brought into contact with a mixture composed of water and of potassium hydroxide in which the potassium hydroxide is present in an amount of between 58 and 86% by weight.

21 Claims, No Drawings

PROCESS FOR THE PREPARATION OF FLUOROOLEFIN COMPOUNDS

FIELD OF THE INVENTION

The subject-matter of the invention is a process for the preparation of fluoroolefin compounds. The invention relates more particularly to a process for the preparation of 1,2,3,3,3-pentafluoropropene (HFO-1225ye) and 2,3,3,3-tetrafluoro-1-propene (HFO-1234yf).

TECHNOLOGICAL BACKGROUND

Hydrofluorocarbons (HFCs) and in particular hydrofluoroolefins (HFOs), such as 2,3,3,3-tetrafluoro-1-propene (HFO-1234yf), are compounds known for their properties of refrigerants and heat-exchange fluids, extinguishers, propellants, foaming agents, blowing agents, gaseous dielectrics, polymerization medium or monomer, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

1,2,3,3,3-Pentafluoropropene (HFO-1225ye) is a synthetic intermediate in the manufacture of 2,3,3,3-tetrafluoro-1-propene (HFO-1234yf).

The majority of the processes for the manufacture of hydrofluoroolefins involve a dehydrohalogenation reaction. Thus, the document WO 03/027051 describes a process for the manufacture of fluoroolefins of formula $CF_3CY=CX_nH_p$, in which X represents a hydrogen atom or a halogen atom chosen from fluorine, chlorine, bromine or iodine and n and p are integers and can independently take the value zero, 1 or 2, provided that (n+p)=2, which comprises bringing a compound of formula $CF_3C(R^1_aR^2_b)C(R^3_cR^4_d)$, with $R^1$, $R^2$, $R^3$ and $R^4$ independently representing a hydrogen atom or a halogen atom chosen from fluorine, chlorine, bromine or iodine, provided that at least one of $R^1$, $R^2$, $R^3$ and $R^4$ is a halogen atom and that at least one hydrogen atom and one halogen atom are situated on adjacent carbon atoms, a and b being able independently to take the value zero, 1 or 2, provided that (a+b)=2, and c and d being able independently to take the value zero, 1, 2 or 3, provided that (c+d)=3, into contact with at least one alkali metal hydroxide in the presence of a phase transfer catalyst.

This document teaches, in Example 2, that, in the absence of a phase transfer catalyst, there is no reaction when 1,1,1,3,3-pentafluoropropane (HFC-245fa) is brought into contact with a 50% by weight aqueous potassium hydroxide (KOH) solution at ambient temperature and under pressure for 24 hours.

In addition, this document teaches a reaction temperature of between −20° C. and 80° C.

The document WO 2008/075017 illustrates the dehydrofluorination reaction of 1,1,1,2,3,3-hexafluoropropane (HFC-236ea) to give 1,2,3,3,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (Test 1). In the presence of a phase transfer catalyst, this conversion is reached after only 2.5 hours and the selectivity is virtually unchanged (Test 4). As indicated in Table 2 of this document, it is necessary to use an organic solvent in order to increase the selectivity for HFO-1225ye.

WO 2007/056194 describes the preparation of HFO-1234yf by dehydro-fluorination of 1,1,1,2,3-pentafluoropropane (HFC-245eb) either with an aqueous KOH solution or in the gas phase in the presence of a catalyst, in particular over a catalyst based on nickel, carbon or a combination of these.

The document Knunyants et al., Journal of the USSR Academy of Sciences, Chemistry Department, "Fluoroolefin Reactions", Report 13, "Catalytic Hydrogenation of Perfluoroolefins", 1960, clearly describes various chemical reactions on fluorinated compounds. This document describes the dehydrofluorination of 1,1,1,2,3,3-hexafluoropropane (236ea) by passing through a suspension of KOH powder in dibutyl ether, to produce 1,2,3,3,3-pentafluoro-1-propene (HFO-1225ye) with a yield of only 60%. This document also describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether with a yield of only 70%.

Furthermore, FIG. 2 on page 51 of Part 2 of the nouveau traité de chimie minerale [New Treatise on Inorganic Chemistry] by P. Pascal, 1963 Ed., shows the appearance of the liquid/solid equilibria of the water and potassium hydroxide system and the measurements are collated in the Table on page 52.

A process for the manufacture of a compound of formula (I) $CF_3-CF=CHX$ in which X represents a hydrogen or fluorine atom, comprising at least one stage of dehydrofluorination of a compound of formula (II) $CF_3-CHF-CHFX$, with a very good selectivity and/or high yield, has now been found.

A subject-matter of the present invention is thus a process for the manufacture of a compound of formula (I) $CF_3-CF=CHX$ in which X represents a hydrogen or fluorine atom, comprising at least one stage of dehydrofluorination of a compound of formula (II) $CF_3-CHF-CHFX$ during which the compound of formula (II) is brought into contact with a mixture composed of water and of potassium hydroxide in which the potassium hydroxide is present in an amount of between 58 and 86% by weight, preferably of between 58 and 69% by weight and advantageously of between 60 and 66% by weight, the said mixture being maintained at a temperature of between 125 and 180° C.

Preferably, the temperature of the water and hydroxide mixture is between 145 and 180° C., and advantageously between 152 and 165° C.

According to one embodiment of the invention, the mixture of water and of hydroxide can be obtained from hydrates of formula $KOH.x.H_2O$, x being between 1 and 2 inclusive.

The dehydrofluorination stage can be carried out in any type of reactor known to a person skilled in the art. Use may be made of a stirred reactor, a static mixer, a reactive column or a nozzle or, very simply, the compound of formula (II) can be bubbled into the said mixture of water and of potassium hydroxide present in a vessel.

In addition to the dehydrofluorination stages, the process comprises a stage of separation of the compound of formula (I), optionally followed by a purification stage.

The operation can be carried out continuously, semicontinuously or batchwise at atmospheric pressure or under pressure, preferably less than 2 bar absolute.

The Applicant Company has observed that the rate of dehydrofluorination of the compound of formula (II) is very high with the mixture of water and of hydroxide as described above and thus particularly advantageous for carrying out the process according to the present invention continuously.

According to a preferred embodiment of the invention, the compound of formula (II) and the mixture composed of water and of hydroxide as defined above are introduced continuously into a reactor, initially charged with this mixture, maintained at the abovementioned temperature and a stream comprising the compound of formula (I) is continuously withdrawn from the gas phase of the reactor. The potassium fluoride formed as by-product can be withdrawn continuously or batchwise from the liquid reaction medium, for example by filtration. The concentration of water in the reaction medium can be kept constant by continuous evaporation of the water formed by the reaction.

When the operation is carried out batchwise or semicontinuously, the KOH/compound of formula (II) molar ratio involved is generally between 2 and 100, preferably between 3 and 20.

The process is very particularly suitable for the manufacture of 2,3,3,3-tetra-fluoropropene by dehydrofluorination of 1,2,3,3,3-pentafluoropropane.

It is also suitable for the manufacture of 1,2,3,3,3-pentafluoropropene by dehydrofluorination of 1,1,1,2,3,3-hexafluoropropane. The 1,2,3,3,3-pentafluoropropene can be in the form of the Z and/or E isomer.

The Applicant Company has discovered that the vinyl trifluoride by-product can be reduced in the case of the dehydrofluorination of HFC-236ea. This by-product becomes negligible when the dehydrofluorination temperature is between 125 and 145° C. and the KOH is present at between 58 and 69% by weight, preferably between 60 and 66% by weight, in the water-KOH mixture.

It can be advantageous to use an inert gas, preferably nitrogen or hydrogen, in the dehydrofluorination stage.

Depending on the conversion desired, the dehydrohalogenation reaction can be carried out in several stages, optionally using several reactors in series, preferably in two stages, optionally using two reactors in series.

The process according to the present invention has the advantage of resulting in high yields, even in the absence of phase transfer catalyst and/or of organic solvent.

EXPERIMENTAL PART

The conversion is defined as the percentage of the compound of formula (II) which has reacted (number of moles of compound of formula (II) reacted/number of moles of compound of formula (II) introduced).

The selectivity is defined as the percentage of the ratio of the number of moles of compound of formula (I) or by-product formed/number of moles of compound of formula (II) which have reacted.

The yield is defined as the percentage of the ratio of the number of moles of compound of formula (I) or by-product formed/number of moles of compound of formula (II) introduced.

Example 1

1005 g of a water and KOH mixture in which the KOH is present at 66% by weight are introduced into a one-liter cylindrical reactor made of stainless steel which is equipped with a heating device and with a device for measuring the temperature of the reaction medium. HFC-236ea, with a flow rate of 150 g/h, and hydrogen, with a flow rate of 12 Nl/h, are bubbled, using a dip pipe, into the medium maintained at 135° C. The gaseous products exit from the reactor via an orifice situated on the lid and are dried via a molecular sieve column and then collected in a stainless steel trap cooled with liquid nitrogen.

The reaction is halted after introduction of 48.3 g of HFC-236ea and the following are obtained:
a conversion of HFC-236ea of 92.7%
a selectivity for HFO-1225ye (E+Z) of 99%
a yield of HFO-1225yeE of 89.9%.

The molar concentration of $CF_2=CFH$ in the liquid collected in the trap at the outlet of the reactor is 0.02%.

Example 2

Use is made of two reactors in series, of the same type as that of Example 1, with the exception of the first reactor, which has a volume of 4 liters, the gas stream resulting from the first reactor feeding the second reactor. 4380 g of a water-KOH mixture with the KOH present at 66% by weight are introduced into the first reactor and 1200 g of a water-KOH mixture with the KOH present at 70% by weight are introduced into the second reactor; the temperature of the medium is maintained at 160° C. HFC-236ea is introduced into the first reactor with a flow rate of 165 g/h and the reaction is halted after introducing 1100 g of HFC-236ea into the first reactor.

A conversion of HFC-236ea of 99.3% and a selectivity for 1225ye (E+Z) of 98% are obtained. The molar concentration of $CF_2=CFH$ in the liquid collected in the trap at the outlet of the reactor is 0.19%.

Example 3

The operation is carried out with the device of Example 1. 1055 g of a water and KOH mixture in which the KOH is present at 86% by weight are introduced into the reactor. HFC-236ea is introduced into the medium, maintained at 165° C., with a flow rate of 150 g/h and the reaction is halted after introducing 1000 g of HFC-236ea. A conversion of HFC-236ea of 98.2% and a selectivity for HFO-1225ye (E+Z) of 95% are obtained. The molar concentration of $CF_2=CFH$ in the liquid collected in the trap at the outlet of the reactor is 1%.

Example 4

The operation is carried out with the device of Example 1. 1000 g of a mixture of water and KOH, the KOH being present at 75% by weight, are introduced into the reactor. HFC-245eb is introduced into the medium, maintained at 160° C., with a flow rate of 150 g/h and the reaction is halted after introducing 276 g of HFC-245eb.

A conversion of HFC-245eb of 83.2% and a selectivity for HFO-1234yf of 99% are obtained. The molar concentration of tetrafluoropropane in the liquid collected in the trap at the outlet of the reactor is 1.5%.

The invention claimed is:

1. Process for the manufacture of a compound of formula (I) $CF_3-CF=CHX$ in which X represents a hydrogen or fluorine atom, comprising at least one stage of dehydrofluorination of a compound of formula (II) $CF_3-CHF-CHFX$ during which the compound of formula (II) is brought into contact with a mixture composed of water and of potassium hydroxide in which the potassium hydroxide is present in an amount of between 58 and 69% by weight the said mixture being maintained at a temperature of between 125 and 180° C.

2. Process according to claim 1, wherein X in the formulae (I) and (II) represents a hydrogen atom.

3. Process according to claim 1, wherein X in the formulae (I) and (II) represents a fluorine atom.

4. Process according to claim 1, wherein the dehydrofluorination is carried out continuously.

5. Process according to claim 1, wherein the dehydrofluorination comprises at least two dehydrofluorination stages.

6. Process according to claim 1, wherein the dehydrofluorination is carried out in the absence of organic solvent and/or phase transfer catalyst.

7. Process according to claim 1, wherein the water and potassium hydroxide mixture is obtained from hydrates of formula $KOH \cdot x H_2O$, x being between 1 and 2 inclusive.

8. Process according to claim 1, wherein the dehydrofluorination comprises a stage of separation of the compound of formula (I) and optionally a purification stage.

9. Process according to claim 1, wherein the temperature of the mixture is between 145 and 180° C.

10. Process according to claim 9, wherein the temperature of the mixture is between 152 and 165° C.

11. Process according to claim 1, wherein the potassium hydroxide is present in an amount of between 60 and 66% by weight.

12. Process for the manufacture of a compound of formula (I) $CF_3—CF\!=\!CHF$, comprising at least one stage of dehydrofluorination of a compound of formula (II) $CF_3—CHF—CHF_2$ during which the compound of formula (II) is brought into contact with a mixture composed of water and of potassium hydroxide in which the potassium hydroxide is present in an amount of between 58 and 86% by weight the said mixture being maintained at a temperature of between 125 and 180° C.

13. Process according to claim 12, wherein the dehydrofluorination is carried out continuously.

14. Process according to claim 12, wherein the dehydrofluorination comprises at least two dehydrofluorination stages.

15. Process according to claim 12, wherein the dehydrofluorination is carried out in the absence of organic solvent and/or phase transfer catalyst.

16. Process according to claim 12, wherein the water and potassium hydroxide mixture is obtained from hydrates of formula $KOH \cdot x H_2O$, x being between 1 and 2 inclusive.

17. Process according to claim 12, wherein the dehydrofluorination comprises a stage of separation of the compound of formula (I) and optionally a purification stage.

18. Process according to claim 12, wherein the temperature of the mixture is between 145 and 180° C.

19. Process according to claim 18, wherein the temperature of the mixture is between 152 and 165° C.

20. Process according to claim 12, wherein the potassium hydroxide is present in an amount of between 58 and 69% by weight and the temperature of the mixture is between 125 and 145° C.

21. Process according to claim 20, wherein the potassium hydroxide is present in an amount of between 60 and 66% by weight.

\* \* \* \* \*